US006342216B1

(12) United States Patent
Fidler et al.

(10) Patent No.: US 6,342,216 B1
(45) Date of Patent: Jan. 29, 2002

(54) THERAPY OF CANCER BY INSECT CELLS CONTAINING RECOMBINANT BACULOVIRUS ENCODING GENES

(75) Inventors: Isaiah J. Fidler, Houston; Zhongyun Dhong, Sugarland; Weixin Lu, Houston, all of TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/271,013

(22) Filed: Mar. 17, 1999

(51) Int. Cl.[7] .................. A61K 48/00; A61K 7/035; C12N 15/63; C12N 15/00; C07H 21/04

(52) U.S. Cl. ............... 424/93.21; 424/93.1; 424/93.2; 424/69.1; 424/69.5; 424/69.51; 424/69.52; 435/320.1; 435/455; 435/456; 435/325; 435/348; 536/23.1; 536/23.5; 536/23.52

(58) Field of Search ............ 424/69.51, 69.52, 424/69.5, 93.21, 93.1, 93.2, 69.1; 435/325, 348, 455, 456, 320.1; 536/23.1, 23.5, 23.52

(56) References Cited

U.S. PATENT DOCUMENTS

| | | | |
|---|---|---|---|
| 4,215,051 A | 7/1980 | Schroeder et al. | 260/346.7 |
| 4,745,051 A | 5/1988 | Smith et al. | 435/68 |
| 4,879,236 A | 11/1989 | Smith et al. | 435/235 |
| 5,077,214 A | 12/1991 | Guarino et al. | 435/240.2 |
| 5,155,037 A | 10/1992 | Summers | 435/240.2 |
| 5,162,222 A | 11/1992 | Guarino et al. | 435/240.2 |
| 5,169,784 A | 12/1992 | Summers et al. | 435/320.1 |
| 5,278,050 A | 1/1994 | Summers | 435/69.1 |
| 5,498,540 A | 3/1996 | Sawyer et al. | 435/240.2 |
| 5,759,809 A | 6/1998 | Iatrou | 435/69.1 |

OTHER PUBLICATIONS

Einhorn, S. & Grander, D. Why do so many cancer patients fail to respond to interferon therapy? J. Interferon and Cytokine Res. 16:275–281, 1996.*

Gariglio, P. et al. Therapeutic uterine–cervix cancer vaccines in humans. Arch. Med. Res. 29:279–284, 1998.*

McCluskie, M.J. et al. Route and method of delivery of DNA vaccine influence immune responses in mice and non–human primates. Mol. Med. 5:287–300, 1999.*

Stokes, A. et al. The expression of the proteins of equine herpesvirus 1 which share homology with herpes simplex virus 1 glycoproteins H and L. Virus Res. 40:91–107, 1996.*

Stokes, A. et al. High level expression of equine herpesvirus 1 glycoproteins D and H and their role in protection against virus challenge in the C3H (H–2K) murine model. Virus Res. 50:159–173, 1997.*

Flannery, C. R. & Sandy, J.D. Aggrecan catabolism in cartilage: Studies on the nature of a novel proteinase (aggrecanase) which cleaves the Glu373–Ala374 bond of the interglobular domain. 39th Annual Meeting of Orthopaedic Research Society, p. 190, 1993.*

Ayres et al., "The Complete DNA Sequence of *Autographa californica* Nuclear Polyhedrosis Virus," *Virology* 202:586–605, 1994.

Bernards, et al., "Effective Tumor Immunotherapy Directed Against An Oncogene–Encoded Product Using A Vaccinia Virgus Vector," *Proc. Nat'l Acad. Sci. USA*, 84:6854–6858, 1987.

Blissard and Rohrmann, "Location, Sequence, Transcriptional Mapping, and Temporal Expression of the gp64 Envelope Glycoprotein Gene of the *Orgyia pseudotsugata* Multicapsid Nuclear Polyhedrosis Virus," Virology 170:537–555, 1989.

Blissard and Rohrmann, "Baculovirus Diversity and Molecular Biology," *Annu. Rev. Entomol.* 35:127–155, 1990.

Carson et al., "Functional Mapping of an AcNPV Immediately Early Gene Which Augments Expression of the IE–1*trans*–Activated 39K Gene," *Virology*, 162:444–451, 1988.

Carson et al., "Transient Expression of the *Autographa californica* Nuclear Polyhedrosis Virus Immediate–Early Gene, IE–N, Is Regulated by Three Viral Elements," *J. Virol.*, 65:945–951, 1991.

Charlton and Volkman, "Penetration of *Autographa californica* Nuclear Polyhedrosis Virus Nucleocapsids into IPLB Sf 21 Cells Induces Actin Cable Formation," *Virology*, 197, 245–254, 1993.

DeGiovanni et al., Immunological an Non–Immunological Influence of H–2K$^b$ Gene Transfection On The Metastatic Abillity of B16 Melanoma Cells, *Int. J. Cancer*, 48:270–276, 1991.

Dinney et al., "Inhibition of Basic Fibroblast Growth Factor Expression, Angiogensis, and Growth of Human Bladder Carcinoma in Mice by Systemic Interferon–α Administration," *Cancer Res.*, 58: 808–814, 1998.

Dong et al., "Suppression Of Tumorigenicity And Metastasis In Murine UV–2237 Fibrosarcoma Cells By Infection With A Retroviral Vector Harboring The Interferon–Beta Gene," *Cancer Immuno. Immunother.*, 46: 137–146, 1998.

(List continued on next page.)

Primary Examiner—Dave Trong Nguyen
Assistant Examiner—Quang Nguyen
(74) Attorney, Agent, or Firm—Fulbright & Jaworski

(57) ABSTRACT

Provided are compositions and methods of use for insect cells comprising baculovirus encoding non–surface expressed proteins and peptides. The claimed invention particularly relates to compositions comprising insect cells containing baculovirus that express cytokines. Such compositions may be administered by, for example, direct intratumoral injection into tumors in mammals, resulting in tumor reduction or recission. Another aspect of the claimed invention concerns methods of promoting resistance to the reoccurence of tumors in mammals who have undergone such tumor recission. In a specific aspect of the claimed invention, the mammals are human subjects presenting with various forms of cancer.

12 Claims, 6 Drawing Sheets

Figure 1:
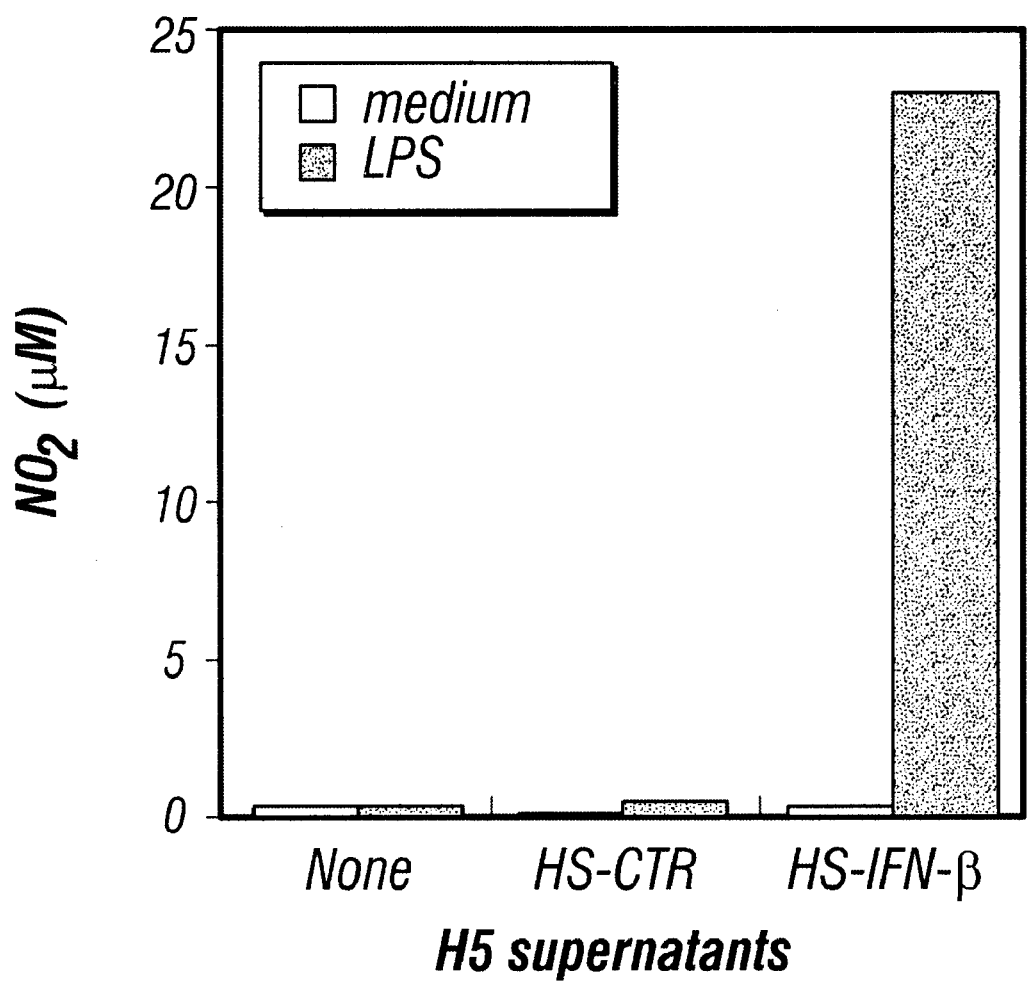

(1 of 6 Drawing Sheet(s) Filed in Color)-

OTHER PUBLICATIONS

Dong et al., "Suppression of Angiogenesis, Tumorigenicity, and Metastasis by Human Prostrate Cancer Cells Engineered to Produce Interferon–β," *Cancer Res.*, 59: 872–879, 1999.

Dranoff et al., "Vaccination With Irradiated Tumor Cells Engineered To Secrete Murine Granulocyte–Macrophage Colony–Stimulating Factor Stimulates Potent, Specific, And Long–Lasting Anti–Tumor Immunity," *Proc. Nat'l Acad. Sci. USA*, 90:3539–3543, 1993.

Elliot et al., "Perspectives on the Role of MHC Antigens in Normal and Malignant Cell Development," *Adv. Cancer Res.*, 53:181–245, 1989.

Estin et al., "Recombinant Vaccinia Virus Vaccine Against The Human Melanoma Antigen P97 For Use In Immunotherapy," *Proc. Nat'l Acad. Sci. USA*, 1052–1056, 1988.

Fabra et al., "Modulation Of The Invasive Phenotype Of Human Colon Carcinoma Cells By Organ Specific Fibroblasts Of Nude Mice," *Differentiation*, 52: 101–110, 1992.

Gohji et al., "Regulation of Gelatinase Production in Metastatic Renal Cell Carcinoma by Organ–specific Fibroblasts," *Jpn. J. Cancer Res.*, 85: 152–160, 1994a.

Gohji et al., "Human Recombinant Interferons–Beta and –Gamma Decrease Gelatinase Production and Invasion by Human KG–2 Renal–Carcinoma Cells," *Intl. J. Cancer*, 58: 380–384, 1994b.

Groner, "Specificity and Safety of Baculoviruses," In: *The Biology of Baculoviruses*, R.R. Ganados and B.A. Federici (Eds.), CRC Press, Boca Raton, Fl., pp. 177–202, 1986.

Guarino and Smith, "Nucleotide Sequence and Characterization of the 39K Gene Region of *Autographa californica* Nuclear Polyhedrosis Virus," Virology, 179:1–8, 1990.

Guarino and Summers, "Nucleotide Sequence and Temporal Expression of a Baculovirus Regulatory Gene," *J. Virol.*, 61:2091–2099, 1987.

Guarino et al., "Complete Sequence and Enhancer Function of the Homologous DNA Regions of *Autographa californica* Nuclear Polyhedrosis Virus," *J. Virol.*, 60:224–229, 1986.

Guarino et al., "Ubiquitin Is Attached to Membranes of Baculovirus Particles by a Novel Type of Phospholipid Anchor," *Cell*, 80:301–309, 1995.

Hooft van Iddekinge et al., "Nucleotide Sequence of the Polyhedrin Gene of *Autographa californica* Nuclear Polyhedrosis Virus," Virology, 131:561–565, 1983.

Hu et al., "Characterization of a Recombinant Vaccinia Virus Expressing Human Melanoma Associated Antigen p97," *J. Virol.*,62 176–180, 1988.

Kaufman et al., "A Recombinant Vaccinia Virus Expressing Human Carcinoembryonic Antigen (CEA)," *Int. J. Cancer*, 48:900–907, 1991.

Kim and Cohen., "MHC Antigen Expression by Melanomas Recovered from Mice Treated with Allogeneic Mouse Fibroblasts Genetically Modified for Interleukin–2 Secretion and the Expression of Melanoma–Associated Antigens," *Cancer Immunol. Immunother.*, 38:185–193, 1994.

Kozuma and Hakuhara, "Fusion Characteristics of a Nuclear Polyhedrosis Virus in Cultured Cells: Time Course and Effect of a Synergistic Factor and pH," *J. Invert. Pathol.*, 63:63–67, 1994.

Kuzio et al., "Nucleotide Sequence of the p10 Polypeptide Gene of *Autographa californica* Nuclear Polyhedrosis Virus," Virology, 139:414–418, 1984.

Martignoni et al., "*Baculovirus of Autographa californica* (Lepidoptera: Noctuidae): a Candidate Biological Control Agent for Douglas–Fir Tussock Moth (Lepidoptera: Lymantriidae)," *J. Econ. Entomol.*, 75:1120–1124, 1982.

Pardoll, et al., "New Strategies for Active Immunotherapy with Genetically Engineered Tumor Cells," *Curr. Opin. Immunol.*, 4:619–623, 1992.

Pardoll, "Cancer Vaccines," *Immunol. Today*, 14:310–316, 1993.

Porgador et al., "H–2$K^b$ Transfection of B16 Melanoma Cells Results in Reduced Tumourigenicity and Metastic Competence," *J. Immunogenet.*, 16:291–303, 1989.

Porgador, et al., "Antimetastatic Vaccination of Tumor–Bearing Mice with Two Types of IFN–γ Gene–Inserted Tumor Cells," *J. Immunol.*, 150:1458–1470, 1993b.

Rosenberg et al., "The Immunotherapy and Gene Therapy of Cancer," *Clin. Oncol.*, 10:180–199, 1992.

Ruby et al., "Recombinant Virus Vectors That Coexpress Cytokines—A New Vaccine Strategy," *Vaccine Res.*, 1:347–356, 1992.

Sibille et al., "Structure of the Gene of tum—Transplantation Antigen P198: A Point Mutation Generates a New Antigenic Peptide," *J. Ex. Med.*, 172:35–45, 1990.

Singh et al., "Interferons α and β Down–Regulate the Expression of Basic Fibroblast Growth Factor in Human Carcinomas," *Proc. Nat'l Acad. Sci USA*, 92: 4562–4566, 1995.

Singh et al., "Cell Density–Dependent Modulation of Basic Fibroblast Growth Factor Expression by Human Interferon–β," *Int. J. Oncol.*, 8:649–656, 1996a.

Singh et al., "Interferon–β Prevents the Upregulation of Interleukin–8 Expression in Human Melanoma Cells," *J. Interferon Cytokine Res.*, 16:577–584, 1996b.

Singh and Fidler, "Systemic Administration of Interferons for Inhibition of Cancer Metastasis,"*In: Clinical Application of Interferons*, (ed. Stuart–Harris and Penney), pp. 391–405, Chapman & Hall, London, 1997.

Smith and Blobel, "The First Membrane Spanning Region of the Lamin B Receptor Is Sufficient for Sorting to the Inner Nuclear Membrane," *J. Cell Biol.*, 120:631–637, 1993.

Tanaka et al., "Role of the Major Histocompatibility Complex Class I Antigens in Tumor Growth and Metastasis," *Ann. Rev. Immunol.*, 6:359–380, 1988.

Thiem and Miller, "Identification, Sequence, and Transcriptional Mapping of the Major Capsid Protein Gene of the Baculovirus *Autographa californica* Nuclear Polyhedrosis Virus," *J. Virol.*, 63:2008–2018, 1989.

Volkman, "The 64K Envelope Protein of Budded *Autographa californica* Nuclear Polyhedrosis Virus," *Curr. Top. Microbiol. Immunol.*, 131:103–118, 1986.

Volkman et al., "Alternate Pathway of Entry of Budded *Autographa californica* Nuclear Polyhedrosis Virus: Fusion at the Plasma Membrane," Virology, 148:288–297, 1986.

Whitford and Faulkner, "A Structural Polypeptide of the Baculovirus *Autographa californica* Nuclear Polyhedrosis Virus Contains O–Linked N–Acetyglucosamine," *J. Virol.*, 66:3324–3329, 1992a.

Whitford and Faulkner, "Nucleotide Sequence and Transcriptional Analysis of a Gene Encoding gp41, a Structural Glycoprotein of the Baculovirus *Autographa californica* Nuclear Polyhedrosis Virus," *J. Virol.*, 66:4763–4768. [Authors' correction (1993) *J. Virol*, 67:2427], 1992b.

Whitford et al., "Identification and Sequence Analysis of a Gene Encoding gp67, an Abundant Envelope Glycoprotein of the Baculovirus *Autographa californica* Nuclear Polyhedrosis Virus," *J. Virol.*, 63:1393–1399, 1989.

Xie et al., "Abrogation of Tumorigenicity and Metastasis of Murine and Human Tumor Cells by Transfection with the Murine *IFN*–$\beta$ Gene: Possible Role of Nirtric Oxide," *Clin. Cancer Res.* 3:2283–2294, 1997.

* cited by examiner

ERADICATION OF UV-2237 TUMORS BY INTRATUMORAL ADMINISTRATION OF LIVE H5IFN-B CELLS

THERAPY OF CANCER BY INSECT CELLS CONTAINING RECOMBINANT BACULOVIRUS ENCODING GENES

1.0 BACKGROUND OF THE INVENTION

1.1 Field of the Invention

The present invention relates generally to the fields of immunology, cancer therapy, molecular biology and cell biology. The present invention relates in particular to compositions and methods for use of insect cells containing non-surface expressed proteins or peptides, encoded by baculovirus expression vectors. Such compositions and methods may be of therapeutic use in the treatment of disease states, such as cancer.

1.2 Description of Related Art

Most progressively growing neoplasms do not provoke immunological responses sufficient to control the growth of malignant cells, despite the fact that tumor cells express antigens which are recognizable as foreign by the immune system of the patient (Sibille et al., 1990).

Tumor-associated antigens (TAAs) capable of being recognized by the cellular immune system (T-cells) have been identified. These antigens (also referred to as tumor associated or T-cell epitopes) include oncogene products activated by mutation and rearrangement (e.g., position 12 mutation in $p21^{ras}$; P210 product of bcr/abl rearrangement); mutated tumor-suppressor gene products (e.g., p53); reactivated embryonic gene products not expressed in adult tissues (e.g., P91A found in the P815 mastocytoma); MAGE 1 (found in melanomas and human breast tumors); tissue specific self-antigens expressed by tumors (e.g., tyrosinase); and a variety of others (Pardoll, 1993). Most tumor cell populations express certain common TAAs, but are heterogeneous with respect to the spectrum of TAAs that they express. Despite the array of tumor-associated T-cell epitopes expressed in tumors, tumor cells remain poorly immunogenic.

An approach to genetic engineering of tumor cells is the use of viral expression vectors to infect tumor cells. Poxvirus technology has been utilized to elicit immunological responses to TAAs in animal models of experimentally-induced tumors. The gene encoding carcinoembryonic antigen (CEA) was isolated from human colon tumor cells and inserted into the vaccinia virus genome (Kaufman et al., 1991). Inoculation of the vaccinia-based CEA recombinant elicited CEA-specific antibodies and an antitumor effect in a mouse model (Id.). The human melanoma TAA, p97, has also been inserted into vaccinia virus and shown to protect mice from tumor transplants (Hu et al., 1988; Estin et al., 1988). Bernards et al. (1987) constructed a vaccinia recombinant that expressed the extracellular domain of the neu-encoded p185 glycoprotein. Mice immunized with this recombinant virus developed a strong humoral response against the neu gene product and were protected against subsequent tumor challenge.

Killing of tumor cells by the immune system is mediated by cytotoxic T-lymphocytes (CTLs). However, the recognition of tumor-associated antigens is restricted by class 1 determinants specified by the major histocompatibility complex (DeGiovanni et al., 1991; Porgador et al., 1989; Kim et al., 1994). Suppression or failure to express MHC class I antigens is one of several documented mechanisms which enable tumor cells to escape T-cell mediated host immunity (Elliott et al., 1990; Tanaka et al., 1988).

Attempts have been made to use cytokines to augment the immune response to tumor-associated antigens. The goal of this strategy is to alter the local immunological environment of the tumor cell to enhance the presentation of T-cell epitopes or the activation of tumor-specific T-lymphocytes (Pardoll, 1993). Various cytokine genes have been introduced into tumor cells. Immunization with neoplastic cells modified to secrete IL-2 (Porgador et al., 1993a; Karp et al., 1993), IFN-α (Porgador et al., 1993b) or GM-CSF (Dranoff et al., 1993), among others (Pardoll et al., 1992; Rosenberg et al., 1992), resulted in the generation of CTLs with cytotoxic activity towards both the cytokine-secreting and non-secreting tumor cells. Experimental animals and a small number of patients with established neoplasms treated with the cytokine-secreting cells survived for prolonged periods, although in most instances tumor growth eventually recurred (Id.).

Recombinant vaccinia viruses also have been used to express cytokine genes (Ruby et al., 1992). Expression of certain cytokines (IL-2, IFN-α) led to self-limiting vaccinia virus infection in mice and, in essence, acted to attenuate the virus. Expression of other cytokines (i.e. IL-5, IL-6) were found to modulate the immune response to co-expressed extrinsic immunogens (Review by Ruby el al., 1992).

Although promising, these observations have not yet resulted in a clinically effective method of eliminating or substantially reducing tumor burden in individuals with cancer. In addition to being expensive, direct in vivo administration of purified cytokines may result in toxic side-effects. Genetically engineering tumor cells to express cytokines in vitro, with subsequent reintroduction into the patient, is difficult, time-consuming, expensive and of unproven clinical efficacy. Gene therapy with human infective viruses engineered to express cytokines has not yet been successfully implemented at the clinical level. One difficulty with this approach is the possible activation of replication-defective viruses by in vivo recombination with naturally occurring human viruses.

A potential solution to this problem involves using baculovirus that has been genetically engineered to express therapeutic proteins. Naturally occurring insect baculovirus infects only arthropods. The host range of insect baculoviruses has been extensively studied and no evidence of infection or pathogenic responses has been identified in non-host insects, plants, vertebrates or humans (Groner, 1986). This feature may make baculovirus an ideal agent to be modified and used for the delivery of drugs, genes, or therapeutics.

2.0 SUMMARY OF THE INVENTION

The present invention addresses deficiencies in the art by disclosing compositions and methods for use of insect cells containing an isolated nucleic acid segment encoding a selected non-surface expressed protein or peptide, for example, a therapeutic protein. A "non-surface expressed protein or peptide" is defined herein as an expressed protein or peptide that is not localized to the cell membrane of the insect cell. In this sense, such proteins or peptides may potentially be secreted into the extracellular environment. Alternatively, the non-surface expressed protein or peptide may be intracellular within the insect cell.

In certain embodiments, the isolated nucleic acid segment is contained within a baculovirus expression vector. The construction of recombinant baculovirus vectors may be accomplished by techniques well known in the art.

In one aspect of the present invention, the non-surface expressed protein or peptide is a cytokine. It is contemplated that almost any cytokine could be used in the practice of the present invention. Classes of cytokines contemplated within the scope of the present invention include interferons, interleukins, tumor necrosis factors and colony stimulating factors. Examples of specific cytokines of potential use in the present invention include interleukin 1 (IL-1), IL-2, IL-5, IL-10, IL-11, IL-12, IL-18, interferon-γ (IF-γ), IF-α, IF-β, tumor necrosis factors-α (TNF-α), and GM-CSF (granulocyte macrophage colony stimulating factor). Such examples are representative only and are not intended to exclude other cytokines known in the art. In a particular embodiment, the cytokine is β-interferon or GM-CSF.

The skilled artisan will realize that the term "protein or peptide" encompasses proteins or peptides with the naturally occurring amino acid sequences of identified proteins or peptides, as well as minor sequence variants of such proteins or peptides. These may, for instance, be minor sequence variants of the polypeptide which arise due to natural variation within the population or they may be homologues found in other species. They also may be sequences which do not occur naturally but which are sufficiently similar that they function similarly and/or elicit an immune response that cross-reacts with natural forms of the polypeptide. Sequence variants can be prepared by standard methods of site-directed mutagenesis or peptide synthesis. Amino acid sequence variants of the polypeptide can be substitutional, insertional or deletion variants. Deletion variants lack one or more residues of the native protein which are not essential for function or immunogenic activity. A common type of deletion variant is one lacking secretory signal sequences or signal sequences directing a protein to bind to a particular part of a cell.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include for example, the changes of: alanine to serine; arginine to lysine; asparagine to glutamine or histidine; aspartate to glutamate; cysteine to serine: glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are introduced, for example, to disrupt a protease cleavage site.

In one aspect, the invention is directed to a method of providing a therapeutic protein to a mammal, comprising preparing a composition comprising insect cells containing an isolated nucleic acid segment encoding a selected non-surface expressed protein or peptide and administering the composition to a mammal. In a preferred embodiment, the mammal is a human subject. In certain embodiments, the insect cells are lyophilized or subjected to freeze-thaw cycles prior to administration. It is contemplated within the scope of the invention that administration of the composition may be accomplished by essentially any route of administration, such as intramuscular, subcutaneous, intraperitoneal, intravascular or intraarterial. For an appropriate composition, administration may occur by oral, nasal, buccal, rectal, vaginal or topical routes.

In a particular embodiment, the composition comprising insect cells may be administered by direct intratumoral injection to a mammal with cancer. The resulting activation of the host immune system, targeted to one or more TAAs, is of utility in reducing or eliminating tumor burden in the subject. This surprising result is of great significance for the clinical treatment of human cancer. Depending upon the specific cytokine selected, other mechanisms of therapeutic treatment are contemplated within the scope of the present invention. For example, β-interferon may interfere with tumor growth by inhibiting angiogenesis. (See Fabra et al., 1992; Ghoji et al., 1994a, 1994b; Singh et al., 1995, 1996a, 1996b; Singh and Fidler, 1997; Dinney et al., 1998, each of which is incorporated herein by reference). In certain embodiments, the administration of compositions comprising insect cells may occur as an adjunct to or in combination with more traditional tumor therapies, such as chemotherapy, radiotherapy or immunotherapy.

The present invention further discloses the unexpected result that subjects whose tumor burdens have been eliminated are resistant to further challenge with cancers expressing the same TAA(s). Yet another surprising aspect of the present invention is that direct tumoral injection of insect cells alone may result in at least a partial suppression of tumor growth. The possibility of an additive or synergistic effect upon the host immune system of presenting both insect cells and expressed therapeutic proteins is contemplated within the scope of the present invention.

The skilled artisan will realize that methods of therapeutic treatment of cancer and methods of immunization of a subject against recurrence of tumors exhibiting the same TAA(s) are contemplated within the scope of the present invention. It further is contemplated within the scope of the present invention that insect cells expressing therapeutic proteins may be used as universal adjuvants in boosting immune system response in various other disease states, such as AIDS or influenza. The skilled artisan will realize that the term "insect cells" includes intact insect cells as well as insect cells that have been lyophilized or subjected to freeze-thaw cycles.

One aspect of the present invention concerns compositions comprising insect cells containing isolated nucleic acid segments encoding a selected non-surface expressed protein or peptide of interest. A variety of different types of insect cells are considered within the scope of the present invention, including cells from *Autographa Californica Bombyx mori, Spodoptera frugiperda, Choristoneura fumiferana, Heliothis virescens, Heliothis zea, Orgyia pseudotsugata, Lymantira dispar, Plutelia xylostella, Malacostoma disstria, Trichoplusia ni, Pieris rapae, Mamestra configurata* and *Hyalophora cecropia*. In a particular embodiment, the insect cell is a *Spodoptera frugiperda* cell or a *Trichoplusia ni* cell. In certain embodiments, such cells may include Sf9 cells or H5 cells (High Five™, Invitrogen, Sorrento, Calif.). In certain embodiments, the isolated nucleic acid segment is incorporated into a baculovirus expression vector. It is contemplated within the scope of the present invention that the baculovirus may be any baculovirus that can be engineered to express an isolated nucleic acid segment encoding a selected non-surface expressed therapeutic protein or peptide. Representative baculoviruses include AcMNPV (*Autographa californica* multinucleocapsid nuclear polyhedrosis virus). BmNPV (*Bombyx mori* nucleopolyhedrosis virus) and pBlueBac (Invitrogen, Sorrento, Calif.). See U.S. Pat. No. 4,215,051 (incorporated herein by reference).

Another embodiment of the present invention encompasses a kit for use in the therapeutic treatment of various disease states, such as cancer, AIDS or influenza, said kit comprising a pharmaceutical composition comprising insect cells containing baculovirus. said baculovirus containing an isolated nucleic acid segment encoding a selected non-surface expressed therapeutic protein or peptide.

3.0 BRIEF DESCRIPTION OF THE DRAWINGS

This application contains at least one drawing executed in color.

The following drawings form part of the present specification and are included to further demonstrate certain aspects of the present invention. The invention may be better understood by reference to one or more of these drawings in combination with the detailed description of specific embodiments presented herein.

FIG. 1. In vitro production of nitric oxide by macrophages in response to stimulation by culture supernatants from H5 insect cells infected with baculovirus expressing IFN-β.

Figure 2A:
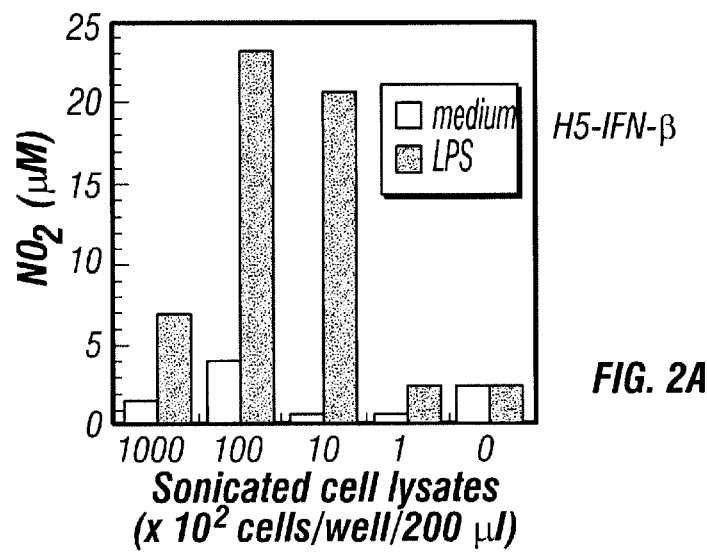

FIG. 2A. In vitro production of nitric oxide by macrophages in response to stimulation by sonicated lysates of H5 insect cells infected with baculovirus expressing IFN-β.

Figure 2B:
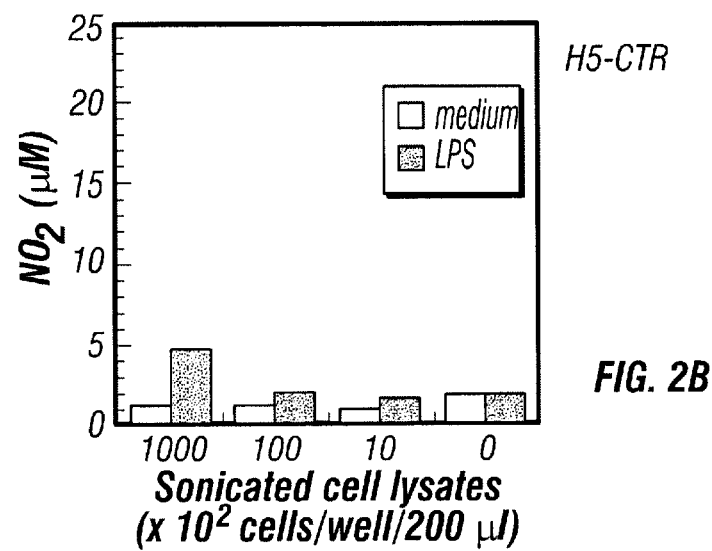

FIG. 2B. Lack of in vitro production of nitric oxide by macrophages in response to sonicated lysates of control H5 insect cells without baculovirus.

Figure 2C:
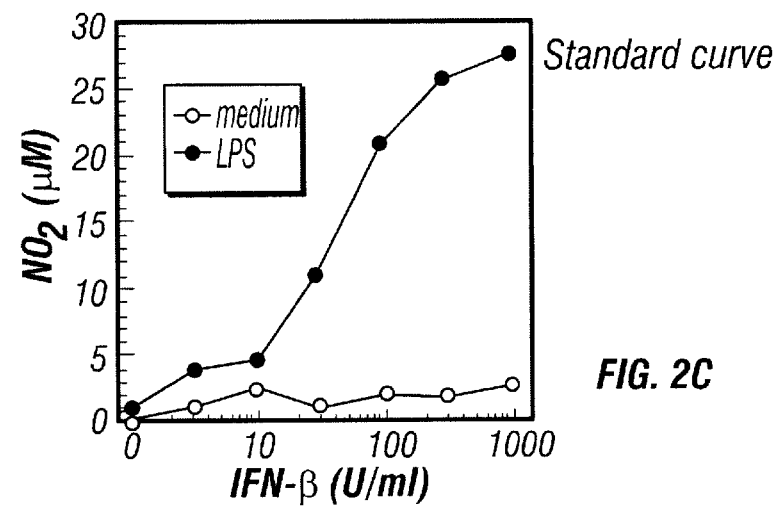

FIG. 2C. Dose-response curve for in vitro production of nitric oxide by macrophages as a function of IFN-β concentration in the supernatant fluids.

Figure 3:
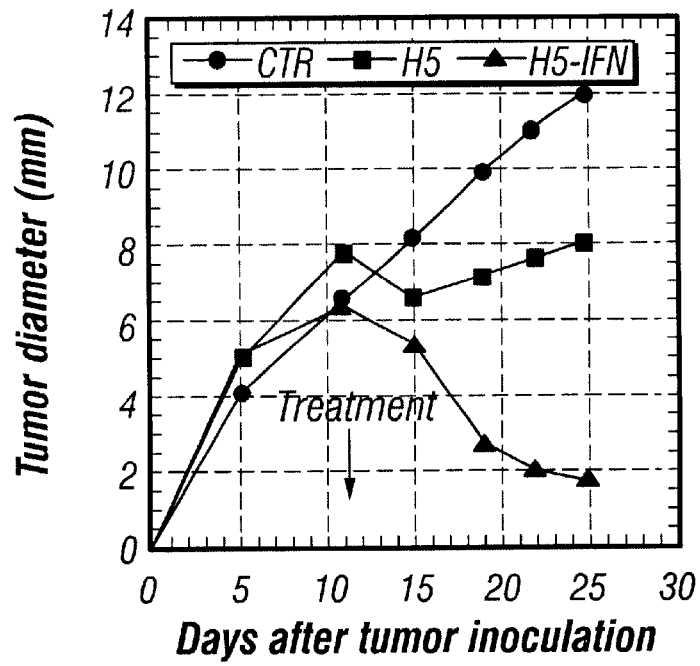

FIG. 3. Effect of intratumoral injection of saline (control), H5 insect cells alone or H5 insect cells containing baculovirus expressing IFN-β on tumor growth. UV-2237M fibrosarcoma cells (2×10$^5$/mouse) were injected subcutaneously (s.c.) into syngeneic C3H/HeN mice. Nine days later the mice were treated by intratumoral injection. H5 cells with baculovirus encoding IFN-β were prepared by infection with 50 µl of baculovirus for 24 hours in T150 flasks.

Figure 4:
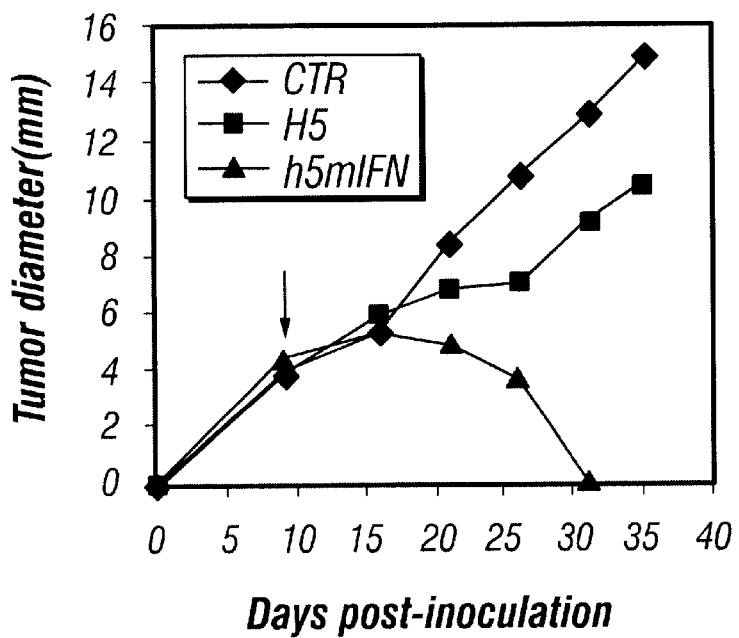

FIG. 4. A repeat of the study shown in FIG. 3, with n=10 mice.

Figure 5:
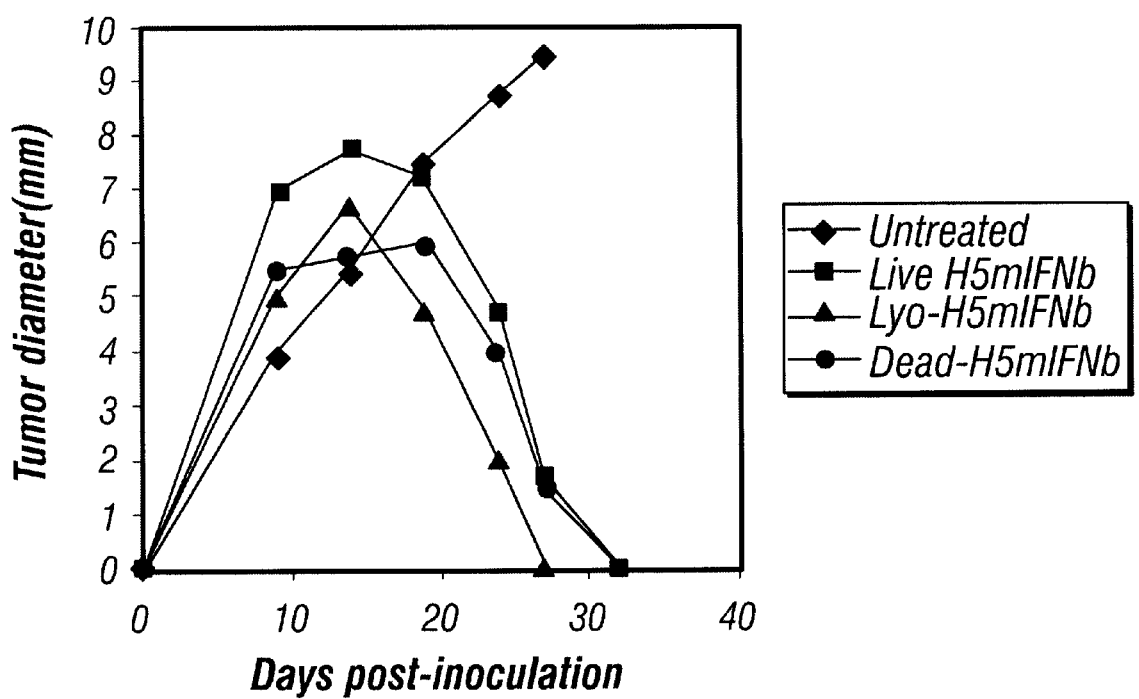

FIG. 5. Effect of intratumoral injection of live, lyophilized and freeze-thawed H5 insect cells containing baculovirus expressing IFN-β on tumor growth of UV-2237M fibrosarcomacells injected s.c. into C3H/HeN mice (n=10).

Figure 6:
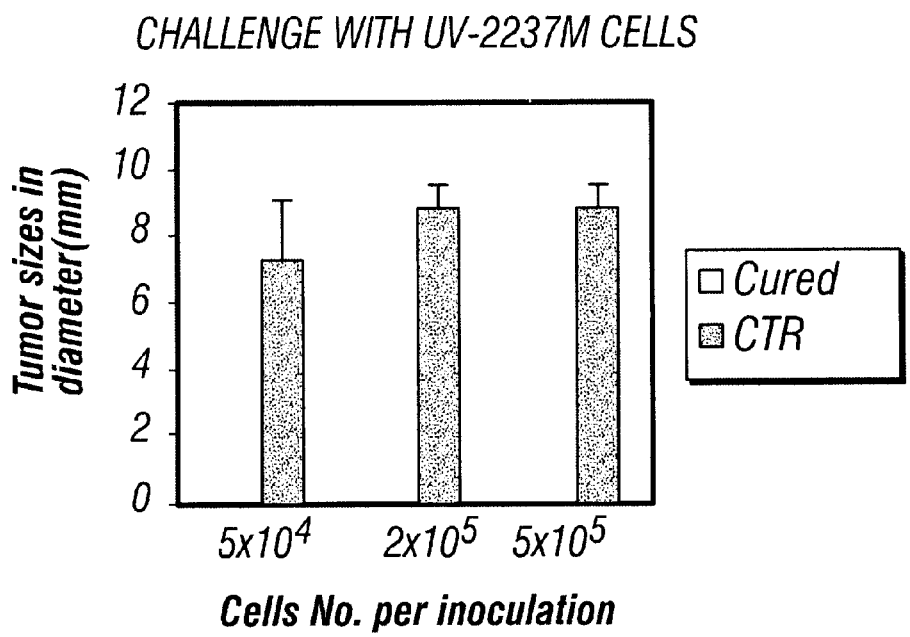

FIG. 6. Generation of systemic immunity in mice "cured" of UV-2237M tumors by intratumoral injection of lyophilized H5 insect cells containing baculovirus expressing IFN-β. C3H/HeN mice (n=10) were injected s.c. with UV-2237M cells. A single intratumorial injection was administered to tumors of 5–6 mm in diameter. Six weeks after tumor regression, the mice were challenged by injection of the indicated amounts of new UV-2237M cells. All control mice developed tumors, while none of the "cured" mice developed tumors.

Figure 7:
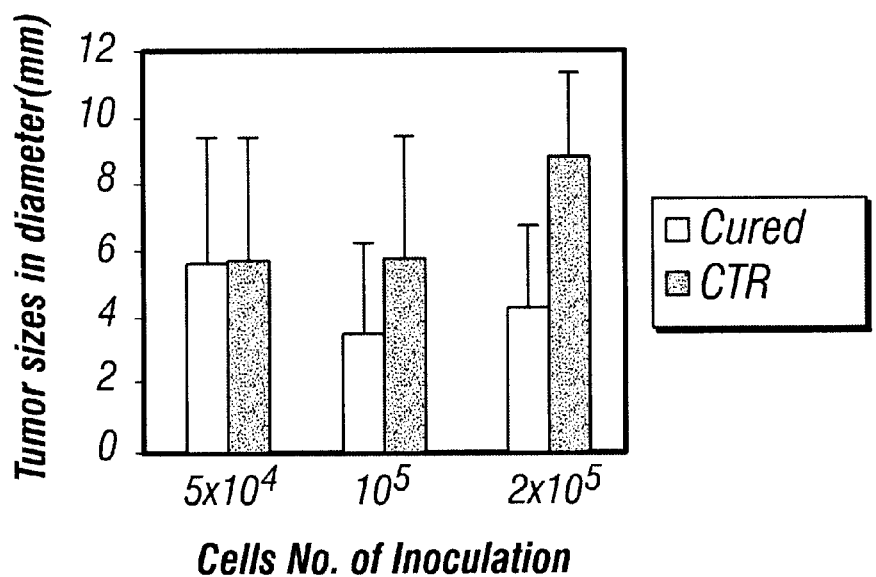

FIG. 7. Systemic immunity in mice "cured" of subcutaneous UV-2237M tumors by intratumoral injection of lyophilized H5 insect cells containing baculovirus expressing IFN-β is specific to tumor type. Mice "cured" of subcutaneous UV-2237M tumors as described in the legend to FIG. 6 were challenged by injection of the indicated amounts of the syngeneic, non-cross-reactive K-1735 melanoma cell line. Both control and "cured" mice developed tumors.

Figure 8:
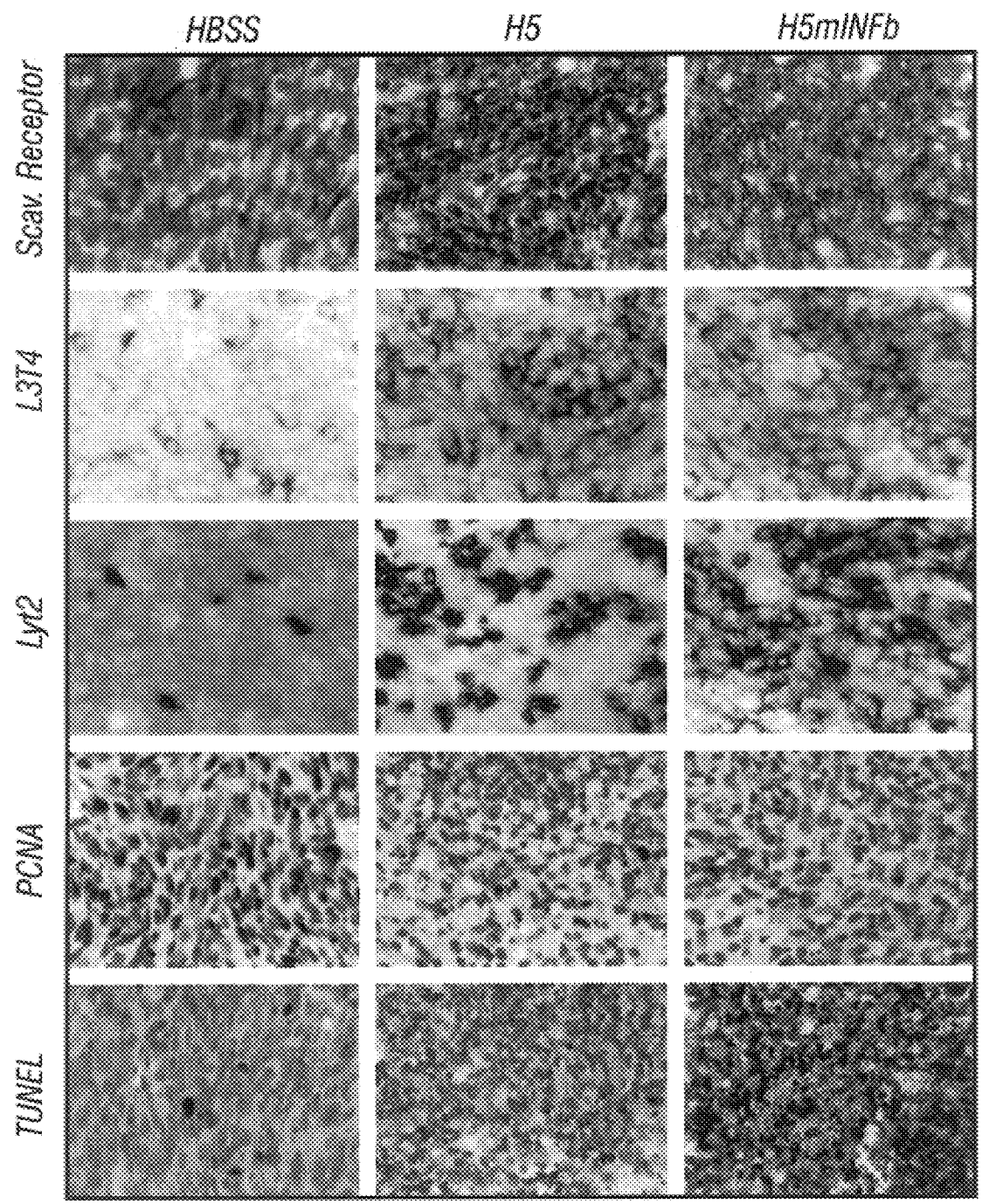

FIG. 8. Immunohistochemistry of regressing UV-2237M s.c. tumors.

4.0 DESCRIPTION OF ILLUSTRATIVE EMBODIMENTS

A number of disease states, such as cancer may in principle be treated by manipulation of the host immune response to the disease (e.g., Xie et al., 1997; Dong et al., 1998, 1999). In practice, deficiencies in the art exist with respect to an effective method for manipulating host immune response. The present invention addresses these deficiencies by providing compositions and methods of use of insect cells comprising baculovirus encoding therapeutic, non-surface expressed proteins or peptides. More particularly, the present invention relates to administering therapeutically effective amounts of such insect cells expressing such proteins or peptides to subjects with disease states such as cancer. In certain embodiments of the present invention, the proteins or peptides are cytokines.

The present invention also concerns methods of inducing tumor regression following administration of insect cells containing non-surface expressed proteins or peptides, for example, cytokines. Another aspect of the present invention concerns methods of preventing the recurrence of cancer in subjects who have been administered such insect cells expressing such proteins or peptides.

4.1 Insect Cells

The term "insect cells" means insect cells from the insect species which are subject to baculovirus infection. For example: *Autographa californica, Bombyx mori, Spodoptera frugiperda, Choristoneura fumiferana, Heliothis virescens, Heliothis zea, Orgyia pseudotsugata, Lymantira dispar, Plutelia xylostella, Malacostoma disstria, Trichoplusia ni, Pieris rapae, Mamestra configurata* and *Hyalophora cecropia*. See U.S. Pat. Nos. 5,498,540 and 5,759,809, incorporated herein by reference. In a particular embodiment, the insect cells are H5 insect cells (Invitrogen, Sorrento, Calif.), derived from *Trichoplusia ni*. Such insect cells may be used in an intact form, or may be used following lyophilization or freeze-thaw cycles.

Insect cells may be cultured according to standard techniques, such as in IPL-41 medium (JRH Biosciences, Inc.) containing 10% fetal calf serum (Hyclone Laboratories, Inc.) as described in U.S. Pat. No. 5,759,809. An alternative procedure for culturing insect cells in media containing fish serum has recently been described. See U.S. Pat. No. 5,498,540, incorporated herein by reference. Cultured insect cells may be transfected with recombinant baculovirus by standard protocols. See, e.g., U.S. Pat. No. 5,759,809, incorporated herein by reference.

4.2 Isolated Nucleic Acid Segments Encoding Cytokines

In various embodiments of the present invention, the insect cells contain isolated nucleic acid segments encoding the production of therapeutic proteins or peptides. Proteins or peptides useful in the application of the present invention include those known as cytokines. Table 1 below provides a listing of cytokines that may be of utility in the practice of the present invention.

TABLE 1

Cytokines

| | | | |
|---|---|---|---|
| IL-1 | IL-2 | IL-3 | IL-4 |
| IL-5 | IL-6 | IL-7 | IL-8 |
| IL-9 | IL-10 | IL-11 | IL-12 |
| IL-13 | IL-14 | IL-15 | β-interferon |
| α-interferon | angiostatin | thrombospondin | endostatin |
| METH-1 | METH-2 | GM-CSF | G-CSF |

The DNA and amino acid sequences of the above-listed proteins or peptides may be obtained from sources well known to those of skill in the art, including GenBank. Isolated nucleic acids encoding many of the proteins listed above may be obtained in the form of pre-existing vectors from standard sources, such as the American Type Culture Collection (ATCC, Gaithersburg, Md.). Alternatively, synthetic genes encoding the proteins or peptides of interest may be chemically synthesized by methods well known in the art, such as on commercially available automated oligonucleotide synthesizers.

As discussed below, a gene encoding a selected therapeutic protein may contain a variety of different bases and yet still produce a corresponding polypeptide that is indistinguishable functionally, and in some cases structurally, from the naturally occurring gene product.

Any reference to an isolated nucleic acid should be read as encompassing a host cell containing that nucleic acid and capable of expressing the product of that nucleic acid. Nucleic acids according to the present invention may encode an entire gene, a domain of a therapeutic protein, or any other fragment of the protein sequence. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene. Such engineered molecules are sometime referred to as "mini-genes."

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression.

It also is contemplated that therapeutic proteins may be represented by natural variants that have slightly different nucleic acid sequences but, nonetheless, encode the same proteins (see Table 2 below).

As used in this application, the term "an isolated nucleic acid segment encoding a non-surface expressed protein or peptide" refers to a nucleic acid molecule that has been isolated free of total cellular nucleic acid. The term "functionally equivalent codon" is used herein to refer to codons that encode the same amino acid, such as the six codons for arginine or serine (Table 2, below), and also refers to codons that encode biologically equivalent amino acids, as discussed in the following pages.

TABLE 2

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The DNA segments of the present invention include those encoding biologically functional equivalent non-surface expressed proteins and peptides. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function.

4.3 Infection with Baculoviral Vectors

In certain embodiments of the invention, the nucleic acid encoding a selected non-surface expressed protein or peptide may be integrated into a baculovirus expression vector. Such vectors are useful tools for the production of proteins for a variety of applications (Summers and Smith, 1987; O'Reilly et al., 1992; also U.S. Pat. No. 4,745,051 (Smith and Summers), U.S. Pat. No. 4,879,236 (Smith and Summers), U.S. Pat. No. 5,077,214 (Guarino and Jarvis), U.S. Pat. No. 5,155,037 (Summers), U.S. Pat. No. 5,162,222, (Guarino and Jarvis), U.S. Pat. No. 5,169,784 (Summers and Oker-Blom) and U.S. Pat. No. 5,278,050 (Summers), each incorporated herein by reference). Baculovirus expression vectors are recombinant insect vectors in which the coding region of a particular gene of interest is placed behind a promoter in place of a nonessential baculoviral gene. The classic approach used to isolate a recombinant baculovirus expression vector is to construct a plasmid in which the foreign gene of interest is positioned downstream of the polyhedrin promoter. Then, via homologous recombination, that plasmid can be used to transfer the new gene into the viral genome in place of the wild-type polyhedrin gene (Summers and Smith, 1987; O'Reilly et al., 1992).

The resulting recombinant virus can infect cultured insect cells and express the foreign gene under the control of the polyhedrin promoter, which is strong and provides very high levels of transcription during the very late phase of infection. The strength of the polyhedrin promoter is an advantage of the use of recombinant baculoviruses as expression vectors because it usually leads to the synthesis of large amounts of the foreign gene product during infection.

*Autographa californica* multinucleocapsid nuclear polyhedrosis virus (AcMNPV) is unusual among baculoviruses because it displays a wider host range than most baculoviruses (Martignoni et al., 1982). AcMNPV is the most extensively studied baculovirus and its genome sequence is known (Ayres et al., 1994). It is distinguished by a unique biphasic life cycle in its lepidopteran host insect (reviewed in Blissard and Rohrmann, 1990). Infection produces high titers of two forms of progeny virus, budded virus (BV) and occlusion derived virus (ODV).

Two routes, adsorptive endocytosis (or viropexis) and direct fusion of BV envelope with plasma membrane, are proposed for entry of BV into cultured cells. Although BV may enter cells by fusion (Volkman et al., 1986; Kozuma and Hukuhara, 1994), the majority of data indicates that the primary route is by adsorptive endocytosis (Charlton and Volkman, 1993).

4.3.1 Expression of Cloned Genes from Baculovirus Promoters and Enhancers

In certain aspects of the present invention, baculovirus vectors which are designed for the expression of a desired gene or genes are required. Thus, particular embodiments may require a selected nucleic acid segment to be operably linked to control sequences, such as promoters and enhancers. In the context of positioning nucleic acid segments and sequence regions in combination, the term "operably linked" will be understood to mean connected so as to form a single, contiguous nucleic acid sequence, wherein the promoters, enhancers and other control sequences are positioned and oriented in a manner to provide optimal expression of the gene. It will be understood that promoters are DNA elements which when positioned functionally upstream of a gene leads to the expression of that gene. Each heterologous gene in the vector of the present invention is functionally positioned downstream of a promoter element.

In transient systems, the gene of interest is introduced into the cell by infection with a recombinant virus, for example baculovirus. In the most widely used baculovirus systems, the gene of interest is under the control of the polyhedrin promoter. The polyhedrin promoter is a very late promoter, which means that the expression of the gene of interest does not start until the late phase of the baculovirus infection. The expression levels are high, but transient as the baculovirus infection eventually leads to cell death.

4.3.2 Baculoviral Promoters and Enhancers

There are four distinct phases of a baculovirus infection, termed immediate-early, delayed-early, late and very late. Therefore, different baculovirus genes may be classified according to the phase of the viral infection during which they are expressed. Also there are a class of genes which have been defined as early genes, which have not been subcatagorized as either immediate-early or delayed-early. Different classes of promoters control each class of gene.

Immediate early promoters are distinguished by needing only host cell factors to drive expression. Examples are the ie1 (Guarino and Summers, 1987), ieN (ie2; Carson et al., 1991) and ie0 promoters.

Delayed early promoters are distinguished by needing only products of the immediate-early genes, in addition to host cell factors to drive expression. Examples are the 39K (Guarino and Smith, 1991) and gp64 (Blissard and Rohrmann, 1989; Whitford et al., 1989) promoters.

Early promoters have not been placed into the specific immediate-early of delayed-early class. Examples include the DA26, ETL and 35K promoters.

Late promoters requires products of the delayed-early and immediate-early genes, as well as other host cell factors, to drive expression. Examples are the gp64 (Blissard and Rohrmann, 1989; Whitford et al., 1989) and capsid (p39, Thiem and Miller, 1989) promoters.

Very late promoters requires a number of baculovirus gene products, in addition to other host cell factors, to drive expression. Examples of promoters from this class are the polyhedrin (Hooft van Iddekinge et al., 1983) and the p10 (Kuzio et al., 1984) promoters. The best characterized and most often used baculoviral promoter is the polyhedrin promoter. The use of the polyhedrin promoter is a preferred embodiment of the present invention.

Enhancers are DNA elements which can be positionally located to enhance transcription from a given promoter. Enhancers which are active in insect cells to drive transcription are preferred in the present invention. Preferred are viral enhancers, and most preferred are baculoviral enhancers. Examples of baculoviral enhancers include hr1, hr2, hr3, hr4 and hr5 (Guarino et al., 1986).

4.4 Marker Genes and Screening

In certain aspects of the present invention, specific cells may be tagged with specific genetic markers to provide information about the infected, transduced or transformed cells. Fherefore, the present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

In other aspects of the present invention, a genetic marker is provided which is detectable by standard genetic analysis techniques, such as DNA amplification by PCR™ or hybridization using fluorometric, radioisotopic or spectrophotometric probes.

Exemplary marker genes encode enzymes such as esterases, phosphatases, proteases (tissue plasminogen activator or urokinase) and other enzymes capable of being detected by their activity, as will be known to those skilled in the art. Contemplated for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells.

Other examples are chloramphenicol acetyltransferase (CAT) which may be employed with a radiolabeled substrate, firefly and bacterial luciferase, and the bacterial enzymes β-galactosidase and β-glucuronidase. Other marker genes within this class are well known to those of skill in the art, and are suitable for use in the present invention.

Another class of marker genes which confer detectable characteristics on a host cell are those which encode polypeptides, generally enzymes, which render their transformants resistant against toxins. Examples of this class of marker genes are the neo gene (Colberre-Garapin et al., 1981) which protects against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302) a gene encoding dihydrofolate reductase, which confers resistance to methotrexate (Alt et al., 1978) and the enzyme HPRT, along with many others well known in the art (Kaufman, 1990).

4.5 Pharmaceutical Compositions and Routes of Administration

Where clinical applications are contemplated, it will be necessary to prepare pharmaceutical compositions of the peptides, proteins, nucleic acids, viruses and cells in a form appropriate for the intended application. Generally, this will entail preparing compositions that are essentially free of endotoxins, as well as other impurities that could be harmful to humans or animals.

One will generally desire to employ appropriate salts and buffers to render peptides, proteins, nucleic acids, viruses or cells suitable for introduction into a patient. Aqueous compositions of the present invention comprise an effective amount of peptides, proteins, nucleic acids, viruses or cells, dissolved or dispersed in a pharmaceutically acceptable carrier or aqueous medium, and preferably encapsulated. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients, such as other anti-cancer agents, can also be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

An effective amount of the peptides, proteins, nucleic acids, viruses or cells is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

Guidance on the amount of insect cells containing baculovirus to inject into tumors is provided in the Examples below. In general, a dose of $1 \times 10^6$ cells per tumor was injected into tumors of 5–6 mm in size. It is expected that the dosage for tumor injection will be determined more by the mass of the tumor than by the size of the patient. Thus, a standard dosage for injection into a 5–6 mm tumor in humans might be approximately $1 \times 10^6$ cells. In the case of injection of cells that have been disrupted by freeze-thaw cycles, injection of an amount of protein equivalent to a dosage of $1 \times 10^6$ cells would be appropriate for a 5–6 mm tumor.

Alternatively, the amount of composition to be administered may be determined by the skilled artisan based upon the concentration of active protein in the composition. The concentration of active protein may be determined by means well known in the art, such as bioassay or by direct measurement of the quantity of specific proteins. (See Remington's Pharmaceutical Sciences, 18th Ed., 1990). Direct measurement of specific proteins may be accomplished by techniques well known in the art, such as ELISA or Western blotting.

The amount of active protein to be administered will vary for the specific protein of interest. For example, dosages of interferon-α to administer to a human subject range from $3 \times 10^5$ IU to $3 \times 10^6$ IU. (See Remington's Pharmaceutical Sciences, 18th Ed., 1990). Standard dosages for interleukin 2 have been reported as 30,000 to 300,000 U/kg/day. (Id.) Standard dosages for other therapeutic proteins are well known in the art.

4.5.1 Parenteral Administration

The active compounds of the present invention will often be formulated for parenteral administration, e.g., formulated for injection via the intravenous, intramuscular, subcutaneous, or even intraperitoneal routes. The preparation of an aqueous composition that contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the particular methods of preparation are vacuum-drying and freeze-drying techniques which yield a powder of the active ingredient plus any additional desired ingredient from a previously sterile-filtered solution thereof.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodcrmoclysis fluid or injected at the proposed site of infusion, (see for example, Remington's Pharmaceutical Sciences, 18th Edition, 1990). Some variation in dosage will necessarily occur depending on the condition of the subject being treated. The person responsible for administration will, in any event, determine the appropriate dose for the individual subject.

4.5.2 Other Routes of Administration

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. The injection can be general, regional, local or direct injection, for example, of a tumor. Also contemplated is injection of a resected tumor bed, and continuous perfusion via catheter. Such compositions would normally be administered as pharmaceutically acceptable compositions, described supra.

The compositions of the present invention are advantageously administered in the form of injectable compositions either as liquid solutions or suspensions; solid forms suitable for solution in, or suspension in, liquid prior to injection also may be prepared. These preparations also may be emulsified. A typical composition for such purposes comprises a 50 mg or up to about 100 mg of human serum albumin per milliliter of phosphate buffered saline. Other pharmaceutically acceptable carriers include aqueous solutions, non-toxic excipients including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

4.6 Combined Therapy with Immunotherapy, Chemotherapy, Biological Therapy or Radiotherapy It is contemplated that a variety of tumors might be treated within the scope of the present invention, including but not limited to cancers of the skin, head, neck, brain, mouth esophagus, stomach, intestines, rectum, vagina, ovaries, cervix, uterus, prostate, testes, breast, lungs, liver, spleen, pancreas, kidneys, bladder, lymphatic system, blood, bone and muscle. Treatment of types of tumors that are considered within the scope of the present invention include but are not limited to sarcomas, adenomas, carcinomas, adenocarcinomas lymphomas, Hodgkin's disease, ncuroblastomas, rhabdomyosarcomas, retinoblastomas, myelomas, melanomas, insulinomas, leukemias and other neoplasias.

Tumor cell resistance to DNA damaging agents represents a major problem in clinical oncology. One goal of current cancer research is to find ways to improve the efficacy of chemotherapy and radiotherapy. One way is by combining such traditional therapies with novel therapies, such as the methods of the present invention. In the context of the present invention, it is contemplated that administration of compositions comprising insect cells, with or without baculovirus encoding therapeutic proteins ("insect cell composition"), could potentially be used in conjunction with chemo- or radiotherapeutic intervention.

To kill cells, inhibit cell growth, inhibit metastasis, inhibit angiogenesis or otherwise reverse or reduce the malignant phenotype of tumor cells, using the methods and compositions of the present invention, one might contact a "target" cell with an insect cell composition and at least one other agent. These treatments would be provided in a combined amount effective to kill or inhibit proliferation of the cell. This process may involve contacting the cells with the insect cell composition and the other agent(s) or factor(s) at the same time. This may be achieved by contacting the cell with a single composition or pharmacological formulation that includes both agents, or by contacting the cell with two distinct compositions or formulations simultaneously, wherein one composition includes the insect cell composition and the other includes the agent.

Alternatively, the insect cell composition treatment may precede or follow the other agent treatment by intervals ranging from min to wk. In such embodiments, one would generally ensure that a significant period of time did not expire between the time of each delivery, such that the agent and insect cell composition would still be able to exert an advantageously combined (e.g., synergistic) effect on the target cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the duration of treatment with only the therapeutic agent significantly, for example, where several days (2, 3, 4, 5, 6 or 7) to several wk (1, 2, 3, 4, 5, 6, 7 or 8) lapse between the respective administrations.

It also is conceivable that more than one administration of either insect cell composition or the other agent will be desired. Various combinations may be employed, where insect cell composition is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

To achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as γ-irradiation, X-rays, UV-irradiation, microwaves, electronic emissions, and the like. A variety of chemical compounds also described as "chemotherapeutic agents," function to induce DNA damage, all of which are intended to be of use in the combined treatment methods disclosed herein. Chemotherapeuticagents contemplated to be of use include, e.g., adriamycin. 5-fluorouracil (5FU), etoposide (VP-16) camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact the tumor cells with an agent in addition to the insect cell composition. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, or mitomycin C. The agent may be prepared and used as a combined therapeutic composition, or kit, by combining it with the insect cell composition, as described above.

Agents that directly cross-link nucleic acids, specifically DNA, are envisaged to facilitate DNA damage leading to a synergistic, antineoplastic combination with insect cell compositions. Agents such as cisplatin, and other DNA alkylating agents may be used.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered intravenouslythrough bolus injections at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. A number of nucleic acid precursors have been developed for this purpose. Particularly useful are agents that have undergone extensive testing and are readily available, such as 5-fluorouracil (5-FU). Although quite toxic, 5-FU is applicable in a wide range of carriers, including topical. However intravenous administration with doses ranging from 3 to 15 mg/kg/day is commonly used.

Other factors that cause DNA damage and have been used extensively include γ-rays, X-rays, and/or the directed delivery of radioisotopes to tumor cells. Other forms of DNA damaging factors also are contemplated such as microwaves and UV-irradiation. It is most likely that all of these factors effect a broad range of damage to DNA, on the precursors of DNA, the replication and repair of DNA, and the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 18th Edition (1990). Some variation in dosage will necessarily occur depending on the condition of the subject being treated. The person responsible for administration will, in any event, determine the appropriate dose for the individual subject. Moreover, for human administration, preparations should meet sterility, toxicity, and general safety and purity standards as required by the FDA Office of Biologics standards.

The regional delivery of insect cell compositions to patients with prostate cancer may be a very efficient method for delivering a therapeutically effective insect cell composition to counteract the clinical disease. Similarly, chemo- or radiotherapy may be directed to a particular, affected region of the subject's body. Alternatively, systemic delivery of insect cell composition and/or the agent may be appropriate in certain circumstances, for example, where extensive metastasis has occurred. The skilled artisan will realize that disruption of H5 cells, for example by freeze-thaw cycles, inactivates the baculovirus without significantly affecting the expressed therapeutic proteins.

In addition to combining insect cell composition-targeted therapies with chemo- and radiotherapies, it also is contemplated that combination with gene therapies may be advantageous. For example, simultaneous targeting of therapies directed toward insect cell compositions and p53 may produce an improved anti-cancer treatment. Any other tumor-related gene conceivably can be targeted in this manner, for example, p21, Rb, APC, DCC. NF-1, NF-2, p16, FHIT, WT-1, MEN-I, MEN-II, VHL, FCC, MCC, ras, myc, neu, raf, erb, src, fms, jun, trk, ret, gsp, hst, bcl and abl. cl 4.7 Kits All the essential materials and reagents required for the various aspects of the present invention may be assembled together in a kit. When the components of the kit are provided in one or more liquid solutions, the liquid solution preferably is an aqueous solution, with a sterile aqueous solution being particularly preferred. In the practice of the present invention, such kit components may comprise isolated insect cells. insect cells containing baculovirus or insect cells containing baculovirus that have been genetically engineered to contain genes encoding therapeutic proteins. In preferred embodiments, the therapeutic proteins are expressed within the insect cell. Such insect cells may be intact or lyophilized. In a preferred embodiment, the insect cells are disrupted by freeze-thaw cycles or other methods that disrupt the structurally integrity of the cell without adversely affecting the protein constituents, including any therapeutic protein(s) of interest.

For in vivo use, the instant compositions may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Additionally instructions for use of the kit components is typically included.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

In Vitro Activation of Macrophages by H5 Cells Infected with Baculovirus Encoding IFN-β

The H5 insect cell line (Invitrogen, Sorrento, Calif.) used in these examples was developed by the Boyce Thompson Institute for Plant Research, Ithaca, N.Y. It was originated from the ovarian cells of the cabbage looper, *Trichoplusia ni*. This cell line doubles in less than 24 h, grows well in monolayer, is adaptable to suspension cultures and serum-free medium and provides 5- to 10-fold higher secreted expression than Sf9 cells. The H5 insect cell line is primarily used for high expression of recombinant proteins.

A recombinant baculovirus encoding mouse interferon-β (IFN-β) gene was developed by the inventors, with a titer of about $5 \times 10^8$ PFU/ml. After infection by baculovirus-IFN-β, H5 cells secreted high levels of IFN-β. To prepare the baculovirus, the full coding region of the mouse IFN-β cDNA was subcloned into the plasmid pxCMV that contains adenoviral genome to derive a shuttle vector pECIFN-β (Graham and Prevec, 1991). The cDNA fragment was then amplified by PCR using the pECIFN-β as template. The restriction enzyme sites for Pst1 and EcoRI were added to the upper (SEQ ID NO:1) and lower (SEQ ID NO:2) primers, respectively. After restrictive digestion with Pst1 and EcoRI, the PCR fragment that contained the mIFN-β coding sequence was subcloned into the baculovirus vector pBlue Bac2A (Invitrogen, San Diego, Calif.) to derive pBac-mIFN-β that was verified by restriction mapping. The pBac-mIFN-β was transfected into SF9 insect cells (Invitrogen San Diego, Calif.) to generate a baculovirus encoding mIFN-β (Bac-mIFN-β) according to the manufacturer's instructions (Invitrogen, San Diego, Calif.). Production of functional mIFN-β was assessed using a bioassay in which IFN-β and LPS activates macrophage to produce nitric oxide (Dong et al., 1998). The stock Bac-mIFN-β produced by SF9 cells was stored at 4° C.

5'-ATCTGCAGAGCCCTCTCCATCAACTA-3' (SEQ ID NO:1)

5'-TTCCAAAACTGAAGAAGGATTCGAAG-3' (SEQ ID NO:2)

For infection of insect cells with baculovirus, H5 insect cells (Invitrogen, San Diego, Calif.) were plated into tissue culture flasks at a density of $4 \times 10^4$ cells/cm$^2$ in 0.15 ml of serum free EXCELL 400 medium (JRH BioSciences, Lenexa, Kans.). After overnight incubation at 28° C., the cells were incubated with 2 plaque-forming units/cell of Bac-mIFN-β for 36 hr. The culture medium was removed and the infected cells were resuspended in phosphate buffered saline (PBS) and used in the therapy experiments described below.

An in vitro assay for macrophage activation was performed according to Dong et al. (1995). Macrophages were exposed to either control medium, supernatant (1:20 dilution) from cultures of H5 insect cells alone or supernatant from cultures of H5 cells infected with baculovirus-IFN-β, then challenged with lipopolysaccharide (LPS). As shown in FIG. 1, macrophage activation only occurred in the presence of H5 cells containing baculovirus-IFN-β. Thus, production of the encoded IFN-β protein was sufficient to cause macrophage activation in vitro. This example further demonstrated that the expressed IFN-β protein was secreted into the supernatant by the baculovirus-infected H5 cells.

Activation of macrophages also was observed using sonicated cell lysates of H5 cells (FIG. 2A). Sonicated control H5 cells had no effect on macrophage activation (FIG. 2B). A standard dose-response curve was observed for macrophage activation by IFN-β (FIG. 2C). However, using sonicated cell lysates a maximum activation of macrophages was observed at a dosage of $10^4$ cells per well in 200 µl of solution (FIG. 2A).

5.2 Example 2

In Vivo Tumor Regression Induced by H5 Cells Infected with Baculovirus Encoding Interferon-β

C3H/HeN mice (n=10) were injected subcutaneously (s.c.) with viable syngeneic UV-2237 M2 fibrosarcoma cells. The UV-2237M cell line (Raz et al., 1981) was derived from spontaneous lung metastases produced by the UV2237 fibrosarcoma, which was originally induced in a C3H/HeN mouse by ultraviolet irradiation (Kripke, 1977). When the tumors reached 5–6 mm in diameter (day 9 of the study), $1 \times 10^6$ untransfected H5 cells (H5) or $1 \times 10^6$ H5 cells transfected with baculovirus encoding IFN-β (H5-IFN-β) were injected into the tumors. Subsequent to this single injection, all tumors (n=10) injected with H5-IFN-β regressed, whereas tumors injected with saline (control) or H5 cells did not (FIG. 3). Although injection with H5 cells alone generally was not sufficient to promote tumor regression, in some cases it caused a decrease in tumor growth rate compared to the control tumors injected with saline (FIG. 3). This example has been repeated at least 4 times, with similar results observed each time. In several of these repetitions, injection of tumors with H5-IFN-β cells was sufficient to promote complete regression of the tumors (FIG. 4). A typical time course for tumor regression is shown below in Table 3.

TABLE 3

Regression of UV-2237M Subcutaneous Tumor Subsequent to a Single Injection with H5 IFN-β Cells
Mean tumor size (mm) ±

| Day | Saline control | H5 control | H5 IFN-β |
|---|---|---|---|
| 9 | 3.6 ± 1.7 | 3.9 ± 1.2 | 4.2 ± 1.2 |
| 16 | 5.6 ± 1.5 | 6.0 ± 1.0 | 5.6 ± 1.1 |
| 21 | 7.7 ± 2.1 | 6.3 ± 1.4 | 4.7 ± 1.2 |
| 26 | 10.1 ± 2.6 | 6.5 ± 3.5 | 2.9 ± 2.9 |
| 31 | 12.5 ± 3.0 | 7.5 ± 4.8 | 2.0 ± 1.1 |
| 35 | 14.8 ± 2.7 | 8.7 ± 5.6$^a$ | 1.9 ± 10$^{b,c}$ |
| incidence | 8/8 | 6/8 | 2/8 |

$^a$UV-2237M cells (2 × $10^5$/mouse) were injected s.c. into C3H/HeN mice. Nine days later, the mice were treated by intratumoral injection of saline, H5, or H5-IFN.
$^b$Infect H5 cells with Bac-IFN: H5 cells in T150 flasks were infected with 50 µl Bac-IFN for 24 h. The cells were harvested and used on treated tumors.
$^c$UV-2237M2 cells (2 × $10^5$) were injected s.c. into syngeneic C3H/HeN female mice (10–12 wks of age). When the tumors reached the diameter of 3–4 mm in diameter (day 9), the mice were randomized into 3 groups: saline control, H5 cells (1 × $10^6$) control, and H5 mIFN-β cells (1 × $10^6$), that were injected once into the tumors. Tumor size was determined using calipers.

5.3 Example 3

Lack of Survival of H5 Cells In Vivo

H5-IFN-β cells were radiolabeled with $^{125}$Iododeoxyuridine. As shown in Table 4, radiolabeled cells survived in culture in vitro for 120 hr with no evidence of radiotoxicity. In contrast, radiolabeled H5-IFN-β cells intravenously injected into mice were eliminated within 48 h. These data indicated that the regression of tumors did not require viable H5-IFN-β cells.

TABLE 4

Survival of [$^{125}$I]IdUrd-labeled H5 cells injection site in vivo and in vitro

| Time | H5 cells radioactivity | | Input radioactivity | Left leg radioactivity | | Input radioactivity |
|---|---|---|---|---|---|---|
| (h) | Median | Range | (%) | Median | Range | (%) |
| 0 | 11741 | (11458, 12024) | 100 | 12534 | | 100 |
| 1 | 4904 | (4797, 5139) | 43 | 6055 | (5907, 6563) | 48 |
| 24 | 6898 | (6371, 6944) | 59 | 500 | (330, 552) | 4 |
| 48 | 8728 | (8163, 8935) | 74 | 16 | (1, 19) | 0.1 |
| 72 | 8527 | (8387, 8545) | 73 | 0 | (0, 0) | 0 |
| 120 | 8680 | (8439, 8879) | 74 | 0 | (0, 0) | 0 |

5.4 Example 4

Eradication of Subcutaneous Tumors by Lyophilized H5-IFN-β Cells

C3H/HeN mice were injected s.c. with viable UV-2237 M2 cells. After the tumors reached 4–5 mm in diameter, groups of mice (n=10) were injected once into the tumors with saline (untreated), $1 \times 10^6$ live H5-IFN-β cells, $1 \times 10^6$ frozen-thawed (3 times) H5-IFN-β cells, or $1 \times 10^6$ lyophilized H5-IFN-β cells.

As shown in FIG. 5, there was essentially no difference in tumor regression induced by live, freeze-thawed (dead) or lyophilized H5-IFN-β cells. This result is significant for potential therapeutic uses of compositions comprising insect cells, as lyophilized or otherwise inactivated insect cells would be advantageous for clinical use. subsequent examples utilized injections of lyophilized H5-IFN-β cells.

5.5 Example 5

Treatment of Mice with H5-IFN-β Cells Induces Systemic Immunity to the Same Tumor C3H/HeN mice were injected s.c. with viable syngeneic UV-2237 M2 fibrosarcoma cells. When the tumors reached 5–6 mm in diameter, the mice were given a single intratumoral injection of saline (untreated), lyophilized preparation of untransfected H5 cells ($1 \times 10^6$/dose), or lyophilized preparation of H5-IFN-β cells ($1 \times 10^6$). All tumors injected with H5-IFN-β cells regressed by day 25 of the study.

Mice cured by this treatment (n=10) were challenged s.c. with $5 \times 10^4$, $2 \times 10^5$, or $5 \times 10^5$ viable UV-2237 M2 cells (n=5). As shown in FIG. 6, none of the cured mice developed tumors, whereas all of the control mice did.

This unexpected result is of great significance for therapeutic treatment of cancer. It demonstrates that within the scope of the present invention, it is possible to immunize mammals using the insect cell compositions described herein, and to provide such mammals with immunity to further challenge by the same tumor. In principle, injection of the claimed insect cell compositions into, for example, an individual with lung cancer, followed by regression of the tumor, should provide that individual with resistance to future development of tumors of the same type. It is not presently known how long such immunity might last. However, methods of periodically boosting immunity against a given disease-associated antigen are known in the art and are within the scope of the present invention.

5.6 Example 6

Systemic Immunity is Tumor Specific

The resistance to the tumor challenge was determined to be specific. Control C3H/HeN mice and C3H/HeN mice cured of s.c. UV-2237M tumors by a single intratumoral injection of lyophilized H5-IFN-β cells were challenged subcutaneously with non-cross-reacting syngeneic K-1735 melanoma cells. Normal (control) mice and mice cured of UV-2237M tumors all developed subcutaneous melanomas (FIG. 7). Thus, the systemic immunity induced by treatment with H5-IFN-β cells does not extend to tumors of different antigenicity.

Two to three months after H5-IFN-β induced regression of UV-2237M tumors, "cured" mice and control normal mice were rechallenged with different numbers of UV-2237M cells or K-1735 melanoma cells. The results presented in Table 5 demonstrate that UV-2237M cells at $5 \times 10^4$, $1 \times 10^5$, or $2 \times 10^5$ cells/inoculum produced tumors in all control normal mice. In contrast, C3H/HeN mice that had been cured of UC-2273M tumors were resistant to rechallenge with UV-2273M cells. The injection of $5 \times 10^4$, $1 \times 10^5$, or $2 \times 10^5$ K-1735 melanoma cells/inoculum produced tumors in all control normal and UV-2273M "cured" mice.

immunogenicity. GM-CSF transduced tumor cells are being used in various preparations of tumor cell vaccines. The injection of GM-CSF at a site of vaccination (tumor cell vaccine preparations) has been shown to increase immunogenicity. presumably by an effect on antigen-presenting cells. These data suggest that GM-CSF can be used to augment immune response.

H5 insect cells infected with baculovirus encoding murine GM-CSF may be admixed with tumor cells and injected s.c. or i.m. (intramuscularly) into mammals. The combination of GM-CSF producing insect cells plus tumor cells (antigen) immunizes the mice against specific TAAs present on the tumor cells. In this embodiment, insect cells producing cytokines act as a universal adjuvant in a vaccine regimen. This adjuvant may be used for treatment of cancer, AIDS, influenza, and other diseases that are amenable to immune system intervention. The insect cells expressing the cytokine may be viable, frozen-thawed or lyophilized. The immunogenicity of the insect cell proteins, coupled with a cytokine stimulates immunity against another protein, such as a tumor antigen, virus or bacterium.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All

TABLE 5

Eradication of subcutaneous UV-2273m tumors by direct injection of H-5 IFN-β cells produces systemic immunity

| Mice | Tumor cells | Incidence | Size | Incidence | Size | Incidence | Size |
|---|---|---|---|---|---|---|---|
| Control | UV-2237M | 5/5 | 7.2 ± 1.9 | 5/5 | 8.9 ± 0.6 | 5/5 | 8.9 ± 0.7 |
| Control | K-1735 | 5/5 | 6.9 ± 4.0 | 5/5 | 6.8 ± 3.0 | 5/5 | 8.4 ± 2.9 |
| H-5 IFN-β | UV-2237M | 0/5 | — | 0/5 | — | 0/5 | — |
| H-5 IFN-β | K-1735 | 5/5 | 6.7 ± 3.4 | 5/5 | 4.3 ± 3.0 | 5/5 | 5.2 ± 2.9 |

Incidence = Number of positive mice/Number of injected mice.
Tumor size = Diameter in mm ± S.D.

5.7 Example 7

Immunohistochemistry of Regressing Tumors

Intratumoral injection of H5-IFN-β can recruit macrophages (scavenger receptor positive cells) and CD-4 and CD-8 positive T cells (L3T4 and Lyt2 positive cells). The injection and lymphoid infiltration associated with inhibition of tumor cell proliferation was reflected in a decrease in proliferating cell nuclear antigen (PCNA) positive cells and in an increase in cells undergoing apoptosis (TUNEL positive cells) (FIG. 8). Thus, injection of H5-IFN-β is associated with activation of the host immune system.

5.8 Example 8

Use of Insect Cells Producing Cytokines in Prophylactic or Therapeutic Vaccines Transduction of weak immunogenic tumor cells with the GM-CSF gene has been shown to enhance antigenicity-such similar substitutes and modifications apparent to those skilled in the art are deemed to be within the spirit, scope and concept of the invention as defined by the appended claims.

6.0 REFERENCES

The following references, to the extent that they provide exemplary procedural or other details supplementary to those set forth herein, are specifically incorporated herein by reference.

U.S. Pat. No. 4,215,051
U.S. Pat. No. 4,430,434
U.S. Pat. No. 4,559,302
U.S. Pat. No. 4,727,028
U.S. Pat. No. 4,745,051
U.S. Pat. No. 4,879,236
U.S. Pat. No. 4,960,704
U.S. Pat. No. 5,077,214

U.S. Pat. No. 5,155,037
U.S. Pat. No. 5,162,222
U.S. Pat. No. 5,169,784
U.S. Pat. No. 5,278,050
U.S. Pat. No. 5,498,540
U.S. Pat. No. 5,759,809
Alt et al., *J. Biol. Chem.*, 253:1357–1320, 1978.
Ayres et al., *Virology* 202:586–605, 1994.
Bernards et al., *Proc. Nat'l Acad. Sci. USA*, 84: 6854–6858, 1987.
Blissard and Rohrmann, *Virology* 170:537–555, 1989.
Blissard and Rohrmann, *Annu. Rev. Entomol.* 35:127–155, 1990.
Carson et al., *Virology*, 162:444–451, 1988.
Carson et al., *J. Virol.*, 65:945–951, 1991.
Chalfie et al., *Science*, 263:802–805.1994.
Charlton and Volkman, *Virology*, 197, 245–254, 1993.
Colberre-Garapin et al., *J. Mol. Biol.*, 150:1–14, 1981.
DeGiovanni et al., *Int. J. Cancer*, 48:270, 1991.
Dinney et al., *Cancer Res.*, 58: 808–814, 1998.
Dong et al., *J. Leukoc. Biol.*, 58: 725–732, 1995.
Dong et al., *Cancer Immunol. Immunother.*, 46: 137–146, 1998.
Dong et al., *Cancer Res.*, 59: 872–879, 1999.
Dranoff et al., *Proc. Nat'l Acad. Sci. USA*, 90:3539–3543, 1993.
Elliott et al., *Adv. Cancer Res.*, 53: 181, 1990.
Estin et al., *Proc. Nat'l Acad. Sci. USA*, 85: 1052–1056, 1988.
Fabra et al., *Differentiation*, 52: 101–110, 1992.
Ghoji et al., *Jpn. J. Cancer Res.*, 85: 152–160, 1994a.
Ghoji et al., *Int. J. Cancer*, 58: 380–384, 1994b.
Graham and Prevec, "Manipulation of adneovirus vectors," In: *Gene Transfer and Expression Protocols*, Vol. 7, pp. 109–128, Humana Press, New Jersey, 1991.
Groner, "Specificity and safety of baculoviruses," In: *The Biology of Baculoviruses*, R. R. Granados and B. A. Federici (Eds.), CRC Press, Boca Raton, Fla., pp 177–202, 1986.
Guarino and Smith, *Virology*, 179:1–8, 1991.
Guarino and Summers, *J. Virol.*, 61:2091–2099, 1987.
Guarino et al., *J. Virol.*, 60:224–229, 1986.
Guarino et al., *Cell*, 80:301–309, 1995.
Hooft van Iddekinge et al., *Virology*, 131:561–565, 1983.
Hu et al., *J. Virol.*, 62: 176–180, 1988.
Karp et al., *J. Immunol.*, 150:896–908, 1993.
Kaufman, *Methods Enzymol.*, 185:537–566, 1990.
Kaufman et al., *Int. J. Cancer*, 48:900–907, 1991.
Kim et al., *Cancer Immunol. Immunother.*, 38:185–193, 1994.
Kozuma and Hukuhara, *J. Invert. Pathol.*, 63:63–67, 1994.
Kripke, *Cancer Res.*, 37: 1395–1400, 1977.
Kuzio et al., *Virology*, 139:414–418, 1984.
Martignoni et al., *J. Econ. Entomol.*, 75:1120–1124, 1982.
O'Reilly et al., In: *Baculovirus Expression Vectors*, W.H. Freeman and Company, N.Y, 1992.
Pardoll et al., *Curr. Opin. Immunol.*, 4:619–623, 1992.
Pardoll, *Immunol. Today*, 14:310–316, 1993.
Porgador et al., *J. Immunogenet.*, 16:291, 1989.
Porgador et al., *Int. J. Cancer.*, 53:471–477, 1993a.
Porgador et al., *J. Immunol.*, 150:1458–1570, 1993b.
Raz et al., *J. Nat'l Cancer Inst.*, 66: 183–189, 1981.
Remington's Pharmaceutical Sciences, 18th Ed., 1990.
Rohrmann, *J. Gen. Virol.*, 73:749–761, 1992.
Rosenberg et al., *Clin. Oncol.*, 10:180–199, 1992.
Ruby et al., *Vaccine Res.*, 4: 347–356, 1992.
Santerre et al., *Gene*, 30:147–156, 1984.
Sibille et al., *J. Ex. Med.*, 172:35–45, 1990.
Singh et al., *Proc. Nat'l Acad Sci. USA*, 92: 4562–4566, 1995.
Singh et al., *Int. J. Oncol.*, 8: 649–656, 1996a.
Singh et al., *J. Interferon Cytokine Res.*, 16: 577–584, 1996b.
Singh and Fidler, "Systemic administration of intererons for inhibition of cancer metastasis, In: *Clinical Application of Interferons*, (ed. Stuart-Harris and Penney), pp. 391–405, Chapman & Hall, London, 1997.
Smith and Blobel, *J. Cell Biol.*, 120:631–637, 1993.
Summers and Smith, "A manual of methods for baculovirus vectors and insect cell culture procedures," *Tex. Agric. Exp. Stn. Bull.*, No.1555, 1987.
Tanaka et al., *Ann. Rev. Immunol.*, 6:359, 1988.
Thiem and Miller, *J. Virol.*, 63:2008–2018, 1989.
Volkman, *Curr. Top. Microbiol. Immunol.*, 131:103–118, 1986.
Volkman et al., *Virology*, 148:288–297, 1986.
Whitford and Faulkner, *J. Virol.*, 66:3324–3329, 1992a.
Whitford and Faulkner, *J. Virol.*, 66:4763–4768. [Authors' correction (1993) *J. Virol.*, 67:2427], 1992b.
Whitford et al., *J. Virol.*, 63:1393–1399, 1989.
Xie et al., *Clin. Cancer Res.*, 3: 2282–2294, 1997.

What is claimed is:

1. A method of treating a mammal having a solid tumor, comprising:

a) providing a pharmaceutical composition comprising insect cells containing a recombinant baculovirus vector encoding a β-interferon or GM-CSF, wherein said β-interferon or GM-CSF is expressed in said cells; and b) administering directly to said solid tumor a therapeutically effective amount of said composition;

wherein said β-interferon or GM-CSF is present in an unpurified form and wherein said administration is effective to reduce or eliminate said solid tumor in said mammal.

2. The method of claim 1, wherein said administration results in the immunization of said mammal against recurrence of said solid tumor.

3. The method of claim 1, wherein said composition is injected directly into said tumor.

4. The method of claim 1, wherein the effective amount of said composition is administered directly to said solid tumor at least twice.

5. The method of claim 1, wherein the effective amount of said composition is administered directly to said solid tumor at least three times.

6. The method of claim 1, wherein said composition comprises between about $10^5$ and about $10^7$ insect cells.

7. The method of claim 1, wherein said insect cells are Spodoptera or Trichoplusia cells.

8. The method of claim 7, wherein said insect cells are *Spodoptera frugiperda* cells.

9. The method of claim 7, wherein said insect cells are *Trichoplusia ni* cells.

10. The method of claim 1, wherein said mammal is a human subject.

11. The method of claim 1, wherein said insect cells are inactivated prior to said administering step.

12. The method of claim 11, wherein said inactivation occurs by subjecting said cells to freeze-thaw cycles.

* * * * *

UNITED STATES PATENT AND TRADEMARK OFFICE
CERTIFICATE OF CORRECTION

PATENT NO.   : 6,342,216 B1
DATED        : January 29, 2002
INVENTOR(S)  : Fidler et al.

It is certified that error appears in the above-identified patent and that said Letters Patent is hereby corrected as shown below:

Column 26,
Line 21, please delete "Spodoptera or Trichoplusia" and insert -- *Spodoptera* or *Trichoplusia* -- therefor.

Signed and Sealed this

Tenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,342,216 B1
DATED         : January 29, 2002
INVENTOR(S)   : Fidler et al.

It is certified that error appears in the above-identified patent and that said Letters Patent is hereby corrected as shown below:

<u>Title page,</u>
Item [75], please delete "Dhong" and insert -- Dong -- therefor.

Signed and Sealed this

Ninth Day of March, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 26
<212> TYPE: DNA
<213> ORGANISM: Mus musculus

<400> SEQUENCE: 1

-continued

```
atctgcagag ccctctccat caacta                                                26

<210> SEQ ID NO 2
<211> LENGTH: 26
<212> TYPE: DNA
<213> ORGANISM: Mus musculus

<400> SEQUENCE: 2
ttccaaaact gaagaaggat tcgaag                                                26
```